United States Patent [19]

Nersesian et al.

[11] 3,959,463

[45] May 25, 1976

[54] HAIR DRESSING COMPOSITIONS CONTAINING A HAIR SUBSTANTIVE QUATERNARY RESIN

[75] Inventors: Ara Nersesian, Livingston; Fred Hubner, Edison; Taras Durbak, Irvington, all of N.J.

[73] Assignee: Bristol-Myers Company, New York, N.Y.

[22] Filed: Jan. 24, 1975

[21] Appl. No.: 543,843

Related U.S. Application Data

[63] Continuation-in-part of Ser. No. 270,409, July 10, 1972, Pat. No. 3,876,760, which is a continuation of Ser. No. 868,892, Oct. 23, 1969, abandoned.

[52] U.S. Cl. .................................. 424/70; 252/316; 424/DIG. 1; 424/DIG. 2; 424/DIG. 4; 424/47; 424/71; 424/170; 424/172; 424/362
[51] Int. Cl.² ............................................ A61K 7/06
[58] Field of Search ................. 424/47, 70, 71, 362, 424/DIG. 1, DIG. 2; 252/316

[56] References Cited
UNITED STATES PATENTS

| | | | |
|---|---|---|---|
| 3,061,519 | 10/1962 | Rosekrans | 424/70 |
| 3,123,640 | 3/1964 | Longley | 260/567.6 |
| 3,123,641 | 3/1964 | Longley | 260/567.6 |
| 3,144,391 | 8/1964 | Goff | 424/71 X |
| 3,210,251 | 10/1965 | Klug | 424/70 X |
| 3,257,281 | 6/1966 | Maeder | 424/71 X |
| 3,427,382 | 2/1969 | Haefele | 424/71 |
| 3,530,215 | 9/1970 | Grief et al. | 424/70 |
| 3,580,853 | 5/1971 | Parran | 424/78 X |

FOREIGN PATENTS OR APPLICATIONS

| | | | |
|---|---|---|---|
| 1,492,597 | 7/1967 | France | 424/78 |

*Primary Examiner*—Albert T. Meyers
*Assistant Examiner*—Vera C. Clarke
*Attorney, Agent, or Firm*—Irving Holtzman; George A. Mentis; David J. Mugford

[57] ABSTRACT

A hair dressing composition comprising a hair substantive quaternary resin to impart hair-holding properties to hair when applied, and a grooming agent; the grooming agent preferably being incompatible with the quaternary resin.

5 Claims, No Drawings

HAIR DRESSING COMPOSITIONS CONTAINING A HAIR SUBSTANTIVE QUATERNARY RESIN

RELATED CASES

This application is a continuation-in-part of application Ser. No. 270,409, filed July 10, 1972, now U.S. Pat. No. 3,876,760 granted Apr. 8, 1975, which in turn is a continuation of application Ser. No. 868,892, filed Oct. 23, 1969, now abandoned.

This invention relates to hair dressing compositions. More particularly, it concerns hair dressing compositions designed to be applied to hair to maintain hair in place, and at the same time to impart thereto certain desirable grooming characteristics, such as lubricity (without greasiness), soft feel, shine, anti-static properties, etc. The properties of these compositions which serve to maintain hair in place is herein referred to as their holding or fixative properties. On the other hand, those properties which give the hair lubricity, soft feel, shine, anti-static properties, etc., are herein described collectively as the grooming and conditioning properties.

Hair dressing compositions of the prior art have, in general, suffered from at least two distinct disadvantages. In those compositions containing a hair fixative (which usually was a film forming resin) dissolved or dispersed in a solvent system, when they were applied to the hair and allowed to dry, tended to cement fibers of hair together giving the hair an overall boardiness. On the other hand, those prior art compositions which leave out the hair fixative and contain only the hair grooming and conditioning agents, as defined above, do not have adequate hair holding properties.

It has now been found that these disadvantages can be avoided by formulating a hair dressing composition comprising, in combination, a hair substantive quaternary resin and a hair grooming agent. The quaternary resin is characterized by its great affinity for hair, which is preferably greater than that which the grooming agent has for hair. The grooming agent is preferably one which is incompatible with the resin and which separates therefrom on the evaporation of a solvent in which they are both dissolved.

Although applicants do not want to be bound by any theory of operation, it is believed that the excellent results obtained with the instant composition are due in large part to the incompatibility of the resin and grooming agent, and their different affinities for hair. When, for example, the compositions are applied in the form of solutions containing the quaternary resin and grooming agent; on the evaporation of the solvent, the quaternary resin, having a greater affinity for hair, coats the same and imparts thereto its fixative properties. The grooming agent, being incompatible with the quaternary resin and having less affinity for hair, separates therefrom. The results appear to be that substantially each hair fiber is provided with a first coat of hair fixative quaternary resin and an over-coat of grooming and conditioning agent. The holding properties of the fixative resin are imparted to the hair fibers. At the same time, they are maintained substantially as uncemented discrete fibers by virtue of the lubricating properties of the over-coat of grooming and conditioning agents. Furthermore, the over-coat of grooming and conditioning agents imparts its other desirable characteristics to the hair, e.g. soft feel, shine, anti-static properties, natural appearance, etc.

It is accordingly an object of the present invention to provide a hair dressing composition capable of simultaneously holding hair in place, and imparting thereto grooming and conditioning characteristics.

It is a further object of the present invention to provide a composition of the aforesaid type which comprises a hair substantive quaternary resin in combination with a hair grooming agent which is incompatible with said hair substantive quaternary resin.

Other and more detailed objects of the present invention will be apparent from the following description and claims.

The compositions of the present invention may take a wide variety of physical forms. Thus, they may take the form of liquids, gels, creams, sticks, pastes, aerosol sprays, etc. As liquids, they may be simple solutions in a variety of solvent systems, such as water, aqueous alcohol, or other organic solvents and mixtures thereof. It may also take the form of an oil-in-water or a water-in-oil emulsion. In the preferred form of this invention, the composition assumes the form of solutions of the active ingredients in an aqueous solvent and particularly, an aqueous alcoholic solvent system. The alcohol is preferably a lower ($C_2$ to $C_6$) alkyl alcohol e.g., ethyl, propyl, isopropyl or butyl alcohol.

A variety of hair substantive quaternary resins known in the prior art are suitable for the purposes of the present invention. One representative class is described in French Pat. No. 1,492,597, which is incorporated herein by way of reference.

These compounds are quaternized cellulose ethers which can be prepared by first etherifying cellulose or alkali cellulose to prepare the ether, e.g., methyl cellulose, hydroxyethyl cellulose, hydroxypropyl cellulose, hydroxypropyl-methyl cellulose, carboxymethyl cellulose or its salts. These may then be quaternized by reacting the respective ethers or mixtures thereof with the halohydrin quaternary salt.

$$\left[ Z-H_2C-\underset{OH}{\overset{}{C}H}-CH_2-\underset{R_2}{\overset{R_3}{\overset{|}{N}}}-R_1 \right]^+ \left[ \frac{Q}{t} \right]^- \qquad I$$

or the epoxy quaternary salts;

$$\left[ H_2C\overset{O}{\overbrace{\qquad}}CH-CH_2-\underset{R_2}{\overset{R_3}{\overset{|}{N}}}-R_1 \right]^+ \left[ \frac{Q}{t} \right]^- \qquad II$$

in which Z above is a halogen, e.g. Cl, Br or I;
R$_1$, R$_2$ and R$_3$ have the values ascribed to them below;
Q is the anion of a strong mineral acid; and
t is a while number equal to the valence of Q.

The resulting compounds may be described generally by the formula:

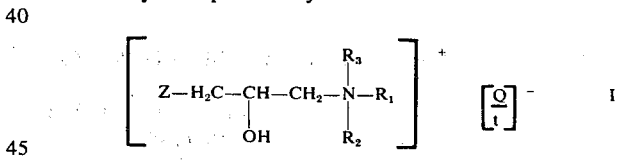

wherein:

Y indicates the degree of polymerization and is a number from 50 to 20,000;

$R_4$, $R_5$ or $R_6$ is a radical of the general formula:

$$-(C_aH_{2a}-O)_m-(CH_2-\underset{\underset{\underset{R_2}{|}}{\underset{R_3-N^+-R_1}{|}}}{\overset{\overset{CH_2}{|}}{CH}}-O-)_n-(C_bH_{2b}O)-_p-(C_cH_{2c})_qR_7 \quad \left[\frac{X}{v}\right]^- \quad \text{IV}$$

in which:

$a$ is a whole number 2 or 3;
$b$ is a whole number 2 or 3;
$c$ is a whole number 1 to 4;
$m$ is a number from 0 to 10;
$n$ is a whole number 0 to 3;
$p$ is a whole number from 0 to 10;
$q$ is zero or 1;
$R_7$ is H or COOMe group in which Me is H, Na, K or $NH_4$;
X is an anion, e.g. $Cl^-$, $Br^-$, $I^-$, sulfate, methylsulfate, sulfonate, nitrate, phosphate, acetate, etc.;
$v$ is a number equal to the valence of X;
$R_1$, $R_2$ and $R_3$ are organic radicals (e.g. alkyl, aryl, etc.) any two or three of which may also constitute together a heterocyclic nitrogen radical. In the general polymer defined in Formula III above, the quaternary group $$-(CH_2-\underset{\underset{\underset{R_2}{|}}{\underset{R_3-N^+-R_1}{|}}}{\overset{\overset{CH_2}{|}}{CH}}-O)_n- \quad \left[\frac{X}{v}\right]^-$$

is present on the average of about 0.1 to 3 quaternary groups per anhydroglucose unit.

$R_1$, $R_2$ and $R_3$ above may be, by way of example, alkyl, aryl, aralkyl, alkaryl, cycloalkyl, alkoxyalkyl or alkoxyaryl. These radicals will usually contain up to 12 carbom atoms. When they are aryl moieties, they are usually hydrocarbon moieties. When they are alkyl moieties they are usually lower alkyl, e.g. 1 to 6 carbon atoms (methyl, ethyl, propyl, butyl, t-butyl, amyl, hexyl, etc.). In the case when they are cycloalkyl, they usually have 5 to 6 carbom atoms in the cycloalkyl ring.

As noted above, any two or three of $R_1$, $R_2$ or $R_3$ may constitute together a heterocyclic nitrogen radical. These will usually contain 5 to 6 atoms in the heterocyclic nucleus and may contain oxygen as well as nitrogen in the heterocyclic ring. By way of illustration, the following may be mentioned: pyridine, α-methylpyridine; 3,5-dimethylpyridine; 2,4,6-trimethylpyridine; N-methylpiperidine; N-ethylpiperidine; N-methylmorpholine or N-ethylmorpholine.

Within the broader class of quaternized cellulose ethers described above, there is a preferred group of materials which are particularly suitable for the purposes of the present invention. These may be described by the formula:

V wherein:

$n = $ a number from 1 to 5;
$x = $ a number from 50 to 20,000 and preferably from 200 to 5000;

A is selected from the group consisting of:

hydrogen; and the quaternary groups;  (1)

$$-CH_2-\underset{\underset{OH}{|}}{HC}-CH_2-\underset{\underset{R_{10}}{|}}{\overset{\overset{R_8}{|}}{N^+}}-R_9. \quad \left[\frac{X}{v}\right]^- \quad (2)$$

$$-CH_2-\underset{\underset{OH}{|}}{HC}-CH_2-N^+\underset{B}{\overset{B}{\bigcirc}} \cdot \left[\frac{X}{v}\right]^- \quad (3)$$

$$-CH_2-\underset{\underset{OH}{|}}{HC}-CH_2-N^+\underset{R_8\ B}{\overset{B\ S}{\bigcirc}} \cdot \left[\frac{X}{v}\right]^- \text{ and } (4)$$

$$-CH_2-\underset{\underset{OH}{|}}{HC}-CH_2-N^+\underset{R_8\ B}{\overset{B\ S\ O}{\bigcirc}} \cdot \left[\frac{X}{v}\right]^-; \quad (5)$$

in which $R_8$, $R_9$ and $R_{10}$ are the same or different and are lower alkyl having from 1 to 6 carbon atoms; B is hydrogen or lower alkyl having from 1 to 6 carbon atoms; and X is an anion such as $Cl^-$, $Br^-$, $I^-$, sulfate, methylsulfate, nitrate, sulfonate, phosphate, acetate, etc; at least one A in said Formula V being one of said quaternary groups; v is a number equal to the valence of X.

One group of hair fixative quaternary resins of special interest in the present invention are Union Carbide's JR-1 Resins. These are advantageous in that they impart holding properties without excessive stiffness; they are effective at low concentrations (0.1%); they form a substantive, elastic film on hair, thus powdering or flaking does not result; they demonstrate good resistance to high humidity conditions; they are soluble in water and can tolerate large concentrations of alcohol (75%); they form a clear film, thus do not dull the hair, and they are compatible with quaternary grooming and germicidal agents.

JR-1 Resins may be described as 2-hydroxypropyl trimethyl ammonium chloride ethers of hydroxyethyl cellulose. The molecular weights of the resins are in the range 200,000 to 2,000,000. The structural formula of the resins can be represented as follows:

1. Alkoxy polyoxyalkylene glycols such as butoxy polyoxypropylene glycols (Ucon LB series); butoxy polyoxyethylene-polyoxypropylene glycols (Ucon 50 HB and 75H series); methoxy polyoxyethylene glycols (Carbowaxes 350, 550, etc.). The preparation of compounds of the "Ucon" series is described in U.S. Pat. No. 2,425,845 to Toussaint et al. A preferred class of materials is also described in U.S. Pat. No. 3,061,519. The latter are described as water soluble lower alkoxy polyoxyalkylene glycols or polyoxyalkylene diols in which the oxyalkylene is a mixture of oxyethylene and oxypropylene in a ratio of about 3:1 to about 1:3 and which have an average molecular weight greater than about 900 and not greater than about 4000. Lower alkoxy is intended to include alkoxy radicals ranging in carbon atom content from 1 to about 6.

2. Polyoxyalkylene glycols such as polyoxypropylene glycols; polyoxyethylene glycols (Carbowaxes 400, 600, 1000, i.e. having a M.W. in the range of about 400–1000, etc.); polyoxypropylene-polyoxyethylene glycols (Wyandotte's Polyol WL-360, Pluronics, etc.).

3. Alkoxy polyoxyalkylene glycol esters (Ucon oleate) and polyoxyalkylene glycol esters (PPG 2000 monooleate).

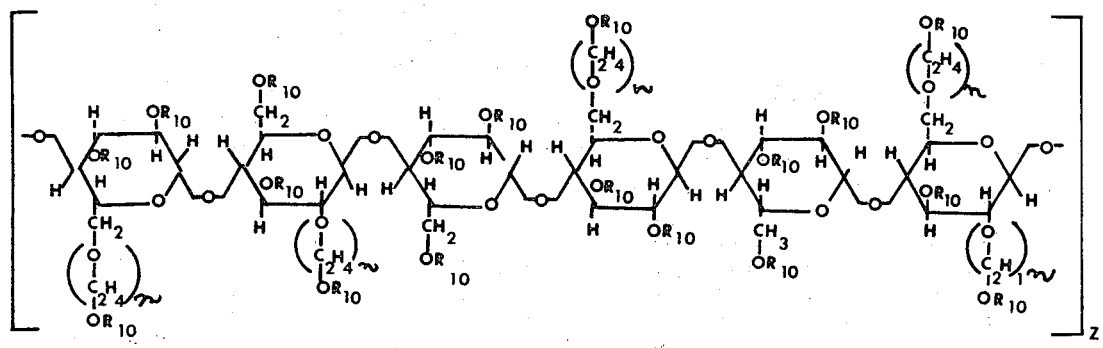

wherein $R_{10}$ is H or

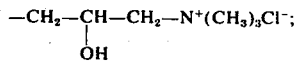

n is 1 to 5 and z is a whole number that represents the degree of polymerization. There are currently two viscosity grades of JR-1 Resins available. One of them is the low viscosity grade JR-1L Resin which has at 25°C a viscosity of (2% aqueous solution) from about 50 to 1000 cps. The other grade is a high viscosity grade (JR-1H Resin) which has a viscosity of (2% aqueous solution) above 1000 cps.

The quantity of quaternary resin that may be incorporated in the compositions of the present invention may vary considerably. In general, however, it will constitute about 0.1% to 7% by weight of the total composition.

A second essential component of the instant compositions is the grooming agent. A wide variety of grooming agents are known in the prior art which may be used for the present purposes. Since the compositions will ordinarily comprise an aqueous base, it is advantageous that these grooming agents be soluble in aqueous solvent systems such as water or aqueous alcohol. By way of illustrating the grooming agents which can be employed in the composition, the following are mentioned which may be used either alone or in combination:

4. Glycerol and trimethylolpropane based triols such as polyoxypropylene triols (Emcol CD-18 known to have a M.W. of about 1500) and polyoxypropylenepolyoxyethylene triols.

5. Polyoxyalkylene ethers suchas polyoxyethylene ethers (Volpos, Brijs) and polyoxypropylene ethers (Procetyl i.e. cetyl alcohol ethers of polyoxypropylene indicated by the manufacturer to have).

6. Diesters of dicarboxylic acid such as diisopropyl adiphate, diisopropyl sebacate, etc.

7. Lanolin and its derivatives such as polyoxyalkylene lanolin ethers (Polychols) and acetylated ethoxylated ester-ethers (Solulan 98).

8. Protein derivatives such as collagen derived hydrolysates (Polypeptide LSN which is known to have a M.W. in the range of from 900–1500, Wilson's WSP X-250 which is known to have a M.W. of about 1000); casein derived hydrolysates (Cascoloids) and protein hydrolysate esters (Promois).

9. Fatty alcohol ethers and fatty acid esters.

10. Higher alcohols (hexadecyl, oleyl, lauryl, cetyl, etc.)

11. Cationic or quaternary compounds, e.g. substituted amine oxides, substituted ammonium halides and substituted imidazolines.

A particularly useful class of grooming agents for the purposes of the present invention are the cationic quaternary ammonium compounds:

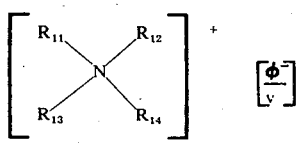 VI wherein $R_{11}$ and $R_{12}$ are alkyl radicals; $R_{13}$ is an aliphatic hydrocarbon group; $R_{14}$ is a polyoxyalkylene radical and $\phi$ is an anion; and v is a number equal to the valence of $\phi$.

In formula VI above, $R_{11}$ and $R_{12}$ can vary in the number of carbon atoms contained in the alkyl chain. Ordinarily these will be lower alkyl chains containing from 1 to 6 and particularly 1 to 2 carbon atoms. Similarly, $R_{13}$ can vary in chain length but will usually be an alkyl or alkenyl group having 1 to 6 carbon atoms.

$R_{14}$ of formula VI above may be a polyoxyalklene radical preferably containing at least 18 carbon atoms and derived from an $\alpha$-epoxide containing at least 3 carbon atoms, e.g., propylene oxide. More specifically, it may be described by the formula:

$$-(CH_2-CH-O-)_n\beta$$
$$\quad\quad\quad\; R_{15}$$
VII wherein $R_{15}$ is hydrogen, or alkyl radical containing 1 to 6 carbon atoms; and n is a whole number from 6 to 40 and $\beta$ is H, acyl radical of a carboxy acid having 2 to 36 carbom atoms or a hydrocarbon radical having 1 to 36 carbon atoms.

When $\beta$ is an acyl radical, it may be derived from any of a number of acids. These include such acids as acetic, lauric, oleic, stearic, palmitic, lanolin fatty acids, etc. When $\beta$ is a hydrocarbon radical, the compound is an ether. This ether likewise maya be derived from a variety of alcohols such as ethyl, lauryl, oleyl, stearyl and lanolin alcohols.

The esters are prepared in the following manner: To a refluxing solution of the acid chloride in anhydrous ethyl ether, the tertiary amine (e.g.

$$\text{CH}_3$$
$$\text{H(OCH}_2\text{CH})_n-\text{N(C}_2\text{H}_5)_2$$

is slowly added. A 10% excess of the acid chloride is employed. The acid chloride is added over a period of 75 minutes and the mixture is maintained at reflux for an additional 2 hours. The reaction mixture is cooled to room temperature and 2N HCl is added. Water is added to the reaction mixture which is then extracted with anhydrous ethyl ether. The acid aqueous residue which contains the tertiary amine ester as the HCl salt is now made basic with concentrated ammonia whereby the free amine ester comes out of solution. This product is extracted with ether and the ether is then driven off leaving the tertiary amine ester. This is then quaternized with methyl chloride by heating a mixture of the amine ester with excess methyl chloride (100% excess) in a sealed tube at 60°C for 18 hours. The tube is then opened and the solvent and excess methyl chloride is evaporated.

The corresponding ethers may be prepared by reacting the tertiary amine alcohol (e.g.

$$\text{CH}_3$$
$$\text{H(O}-\text{CH}_2-\text{CH}-)_n\text{N(C}_2\text{H}_5)_2$$

with a fatty alcohol, e.g. lauryl alcohol, ethyl alcohol or stearyl alcohol in the presence of a small quantity of a catalyst (e.g. p-toluene sulfonic acid). Excess HCl is added and the reaction mass is extracted with ethyl ether. The aqueous acidic residue is made basic with concentrated ammonia and reextracted with ether. The ether is then evaporated and the amine ether is quaternerized with methyl chloride in a fashion similar to that described above for the preparation of the quaternized amine ester.

The radical $\phi$ of formula VI can be any negative or salt-forming radical as, for instance, halide such as chloride, bromide and iodide; hydroxy; sulfate, alkyl sulfate (methosulfate or ethosulfate); nitrate; phosphate; acetate; formate; carbonate; lower alkyl (1 to 4 carbon atoms) sulfonates; and the like. Of particular interest are those of the cation-active surface active agents in which the anion is chloride, bromide, methyl chloroacetate, methosulfate, and ethosulfate.

Cationic surface active quaternary ammonium grooming compounds that are useful for the purpose of the present invention and the manner of preparing the same are described in U.S. Pat. Nos. 3,123,640; 3,123,641 and 3,141,904 which are incorporated herein by way of reference. Of special interest are compounds described by the formula:

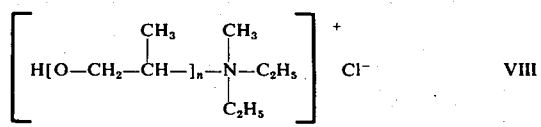 VIII in which n has an average value of about 8, 25 and 40 respectively and whose apparent molecular weights are 600, 1600 and 2500 respectively.

A number of the cationic surface active quaternary ammonium compounds mentioned above are available commercially. By way of example, mention may be made of products sold under the trade designations EMCOL CC-9, EMCOL CC-36 and EMCOL CC-42.

The quantity of grooming agent incorporated in the present composition also will obviously vary with the intended purpose. In general, however, this will constitute between 1.0 to 60% by weight of the total composition.

Optimum results are obtainable by maintaining the grooming agent at a higher level than the quaternary resin in the composition. The preferred ratio is 1 part of quaternary resin to 10 to 30 parts of grooming agent.

It is sometimes advantageous to modify the properties of the aforesaid composition by including therein one or more auxiliary resins. A number of resins are known in the prior art which could serve as auxiliary resins. In this connection, mention may be made of the following:

AUXILLIARY RESINS

1. Polyvinyl pyrrolidone (PVP) and its derivatives such as alkylated polyvinylpyrrolidone (Ganex) polyvinylpyrrolidone-vinyl acetate copolymers (PVP/VA), etc.

2. Hydroxyalkyl cellulose derivatives such as hydroxyethyl cellulose (Cellosize, Natrosol); hydroxypropyl cellulose (Klucel); hydroxymethylhydroxypropyl cellulose (Methocel), etc.

3. Polyvinyl alcohols (Elvanol).
4. Polyoxyethylene resins(Polyox).

The above list is given by illustration only and does not enumerate all possible auxilliary resins.

The quantity of auxiliary resins that may be employed can also vary considerably. In general, it may constitute between 0% to about 3% by weight of the total composition.

In addition to the aforesaid ingredients, if desired, other conventional ingredients commonly found in hair grooming preparations may be included in the present composition. These include such agents such as slip agents, plasticizers, germicides, fragrance, colors, solvents and other vehicles, etc. By way of illustration, the following may be mentioned:

1. Plasticizers which are compatible with the resin may be incorporated to control the hardness and elasticity of the resin film are as follows: glycerol, glycols (propylene, dipropylene, polyoxyethylene, etc.), phthalic acid esters, quaternary compounds (stearyl dimethyl benzyl ammonium chloride, etc.) and others as used in the art.

2. Germicides and preservatives such as quaternary nitrogen compounds (benzethonium chloride, cetyl pyridinum chloride, etc.); p-hydroxy benzoate esters (Parabens), chlorinated phenols (e.g. hexachlorophene) etc.

3. Thickening agents such as carboxyvinyl polymer (Carbopol).

4. Rubefacients such as methyl nicotinate, capsicum tincture, dipropylene glycol salicylate, etc.

5. Keratolytic agents such as salicylic acid, resorcinol, sulfur, etc.

6. Antidandruff agents such as Zinc Omadine (i.e., zinc pyrithione $C_{10}H_8N_2O_2S_2Zn$), selenium sulfide, biphenamine hydrochloride, etc.

7. Hair coloring agents.
8. Fragrances.
9. Color.

The preferred form of this invention comprises an aqueous alcoholic solution of quaternary resin and grooming agent. Table I below sets the general range of ingredients and the preferred concentrations in this aspect of the invention.

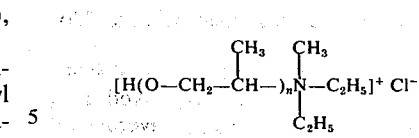

Emcol CC-9; n in above formula has an average value of 8; average M.W. = 600;

Emcol CC-36; n in above formula has an average value of 25; average M.W. = 1600;

Emcol CC-42; n in above formula has an average value of 40; average M.W. = 2500;

3. Grooming Agent No. 2000: Butoxypolyoxyethyleneoxypropylene glycol having a M.W. of 2650 and a viscosity of 2000 Saybolt Universal seconds at 100°F; the oxyethylene and oxypropylene are in equal parts;

4. Grooming Agent No. 450: Polyoxyethyleneoxypropylene diol having a M.W. of 990 and a viscosity of 450 Saybolt Universal seconds at 100°F; the ratio of oxyethylene to oxypropylene is 3:1;

5. Triol 700: polyoxypropylene triol having an average M.W. of about 700 (reaction product of glycerine and propylene oxide);

6. Emcol CC-9 Laurate, Emcol CC-9 Stearate:

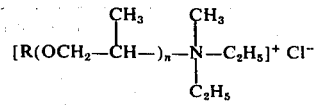

Emcol CC-9 Laurate, n in the formula above has an average value of about 8 and R is lauroyl, i.e.

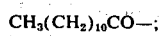

Emcol CC-9 - Stearate; n in the formula above has an average value of about 8 and R is stearyl.

7. Freon 12 — Dichlorodifluoromethane;

8. Carbowax 400 — Polyoxyethyleneglycol M.W. 400;

9. Polyoxyethylene glycol (400) Monooleate — The monooleate of polyoxyethylene glycol having an M.W. of 400;

10. Ucon 50 HB 600 — Butoxypolyoxyethylenepolyoxypropylene glycol having an polyoxyethylene to polyoxypropylene ratio of 1:1 and a viscosity of 660 Saybolt Universal seconds at 100°F. M.W. about 2000;

11. Ucon LB 1715 — Butoxypolyoxypropyleneglycol having a viscosity of 1715 Saybolt Universal seconds at 100°F; M.W. about 2000;

TABLE I

| INGREDIENTS | PERCENT BY WEIGHT | |
|---|---|---|
| | GENERAL RANGE | PREFERRED CONCENTRATION |
| Quaternary Resin | 0.1 - 7.0 | 0.3 |
| Ethyl alcohol | 0.0 - 75.0 | 50.0 |
| Water | 25.0 - 98.0 | 44.7 |
| Grooming agents | 1.0 - 60.0 | 5.0 |
| Auxilliary agents | q.s. | q.s. |

The following Examples are further illustrative of the present invention. It is to be understood, however, that the invention is not limited thereto. In these Examples when the following terms appear, they have the meaning described below:

1. JR-IL Resin: For description see specification above;

2. Emcol CC-9; Emcol CC-36 and Emcol CC-42

12. Methocel 60 HG 4000; hydroxypropyl methylcellulose ether having 28% to 30% by weight of methoxy substituents and 7% to 12% by weight of hydroxypropyl substituents; the degree of substitution with methoxy and hydroxypropyl substituents is from 1.68 to 1.82 and from 0.17 to 0.3 respectively; viscosity 3500–5600 cps. (2% aqueous solution at 20°C). (See U.S. Pat. No. 3,427,382).

13. Carbopol 940: (purified form of Carbopol 934) water soluble polymer of acrylic acid cross linked with 1% of a polyallyl ether of sucrose having an average of about 5.8 allyl groups for each molecule of sucrose (See U.S. Pat. No. 3,133,865).

14. P.V.P.: See THE MERCK INDEX, eighth edition, page 849–850.

15. Stepans Polypeptide AAS-20% Active: This is an alcohol soluble base hydrolyzed collagen protein derivative. (See "Protein, Some New Derivatives" by Richard Riso — Proceedings of the Toilet Goods Association No. 42, pages 36–39, December, 1964.

EXAMPLE 1

| INGREDIENT | PERCENT BY WEIGHT |
|---|---|
| JR-1L Resin | 0.30 |
| Emcol CC-36 | 4.00 |
| Diisopropyl adipate | 1.00 |
| Dipropylene glycol | 0.70 |
| Benzethonium chloride | 0.10 |
| *Perfume | 0.40 |
| *Color (.1% aqueous solution) | 0.37 |
| Ethyl alcohol (95% aq.) | 50.00 |
| Water | 43.13 |
|  | 100.00 |

*The perfume and color may be omitted from this composition if desired, in which event they are replaced by an equal quantity of water.

EXAMPLE 1A to 1E

The composition similar to that of Example 1 is prepared excepting that for the JR Resin of Example 1 an equal quantity of the product of Example 1 of French Pat. No. 1,492,597 is utilized as the quaternary resin. In a similar fashion, a series of compositions are prepared similar to that of Example 1 above excepting that each contains an equal quantity of the material prepared by the Examples of 2, 5, 7, 9 and 12 of French Pat. No. 1,492,597 in place of the JR-1L Resin of Example 1 as the quaternary resin.

The following Examples 2 through 19 are given in tabular form. They illustrate other aqueous or aqueous alcoholic systems in which the quaternary resin and the grooming agents are dissolved in the solvent system.

present in solution. In these examples different quaternary grooming agents are employed:

| INGREDIENT | PERCENT BY WEIGHT EXAMPLE | | |
|---|---|---|---|
|  | 20 | 21 | 22 |
| JR-1L Resin | 0.3 | 0.3 | 0.3 |
| Emcol CC-9 | 5.0 | — | — |
| Emcol CC-36 | — | 5.0 | — |
| Emcol CC-42 | — | — | 5.0 |
| Ethyl Alcohol | 50.0 | 50.0 | 50.0 |
| Water | 44.7 | 44.7 | 44.7 |
| Perfume, Color, etc. | q.s. | q.s. | q.s. |

The following examples also illustrate the use of certain quaternary grooming agents in combination with the quaternary resin.

| INGREDIENT | PERCENT BY WEIGHT EXAMPLE | |
|---|---|---|
|  | 23 | 24 |
| Emcol CC-9 Laurate | 15.0 | — |
| Emcol CC-9 Stearate | — | 5.0 |
| JR-1L Resin | 1.0 | 0.3 |
| Ethyl Alcohol | 40.0 | 50.0 |
| Water | 44.0 | 44.7 |
| Perfume, Color, etc. | q.s. | q.s. |

The following example illustrates the use of a substituted amine oxide-type grooming agent.

| INGREDIENT | PERCENT BY WEIGHT EXAMPLE |
|---|---|
|  | 25 |
| Lauryl amine oxide | 5.0 |
| JR-1L Resin | 0.3 |
| Ethyl alcohol | 50.0 |
| Water | 44.7 |
| Perfume, color, etc. | q.s. |

The following examples illustrate the use of auxilliary resin in accordance with the present invention.

| INGREDIENT | PERCENT BY WEIGHT EXAMPLE | |
|---|---|---|
|  | 26 | 27 |
| JR-1L Resin | 0.5 | 0.5 |
| Methocel 60 HG 4000 | — | 0.5 |

TABLE 2

| INGREDIENT | PERCENT BY WEIGHT | | | | | | | | | | | | | | | | | |
|---|---|---|---|---|---|---|---|---|---|---|---|---|---|---|---|---|---|---|
|  | Ex. 2 | Ex. 3 | Ex. 4 | Ex. 5 | Ex. 6 | Ex. 7 | Ex. 8 | Ex. 9 | Ex. 10 | Ex. 11 | Ex. 12 | Ex. 13 | Ex. 14 | Ex. 15 | Ex. 16 | Ex. 17 | Ex. 18 | Ex. 19 |
| PRODUCT of Ex. 1 French Patent 1,492,597 | 0.1 | 0.5 | 1.0 | 2.0 | 0.3 | 0.3 | 0.3 | 0.3 | 2.85 | 0.3 | 0.3 | 0.3 | 0.3 | 0.3 | 0.3 | 0.3 | 0.3 | 0.3 |
| WATER | 44.9 | 44.5 | 44.0 | 43.0 | 44.7 | 47.7 | 39.7 | 94.7 | 92.15 | 44.7 | 74.7 | 49.7 | 29.7 | 29.7 | 24.7 | 44.7 | 44.7 | 44.7 |
| ETHYL ALCOHOL (95%) | 50.0 | 50.0 | 50.0 | 50.0 | 50.0 | 50.0 | 50.0 | — | — | 30.0 | — | — | 65.0 | 60.0 | 60.0 | 50.0 | 50.0 | 50.0 |
| PRODUCT OF EX. 1 U.S. Patent 3,123,641 | 5.0 | 5.0 | 5.0 | 5.0 | 5.0 | 2.0 | 10.0 | — | — | — | — | — | — | — | — | 2.5 | 2.5 | 2.5 |
| GROOMING AGENT No. 2000 | — | — | — | — | — | — | — | 5.0 | 5.0 | 25.0 | 25.0 | 50.0 | — | — | — | 2.5 | — | — |
| GROOMING AGENT No. 450 | — | — | — | — | — | — | — | — | — | — | — | — | 5.0 | 10.0 | 15.0 | — | 2.5 | — |
| Triol-700 | — | — | — | — | — | — | — | — | — | — | — | — | — | — | — | — | — | 2.5 |

The following examples further illustrate aqueous alcoholic systems in which the active ingredients are

| INGREDIENT | PERCENT BY WEIGHT EXAMPLE | |
|---|---|---|
| | 26 | 27 |
| PVP | 0.5 | — |
| Emcol CC-36 | 5.0 | 5.0 |
| Ethyl alcohol | 50.0 | 30.0 |
| Water | 44.0 | 64.0 |
| Perfume, color, etc. | q.s. | q.s. |

The following example illustrates the present invention in which it takes the form of a gel.

| INGREDIENT | PERCENT BY WEIGHT EXAMPLE 28 |
|---|---|
| Carbopol 940 | 1.0 |
| JR-1L Resin | 0.5 |
| Triethanolamine | 1.5 |
| Emcol CC-36 | 5.0 |
| Water | 62.0 |
| Ethyl alcohol | 30.0 |
| Perfume, color, etc. | q.s. |

The following examples illustrate the present invention in the form of an aerosol spray.

| INGREDIENT | PERCENT BY WEIGHT EXAMPLE | |
|---|---|---|
| | 29 | 30 |
| JR-1L Resin | 0.3 | 0.3 |
| Emcol CC-36 | 4.0 | 4.0 |
| Water | 25.7 | 30.7 |
| Ethyl alcohol | 30.0 | 30.0 |
| Freon 12 | 40.0 | — |
| Isobutane | — | 35.0 |
| Perfume, color, etc. | q.s. | q.s. |

The following examples are a miscellaneous group of examples illustrating a variety of aspects of the present invention.

| INGREDIENT | PERCENT BY WEIGHT EXAMPLE | | | | |
|---|---|---|---|---|---|
| | 31 | 32 | 33 | 34 | 35 |
| JR-1L Resin | 0.3 | 0.3 | 0.3 | 0.3 | 0.3 |
| Ethyl alcohol | 50.0 | 65.0 | 50.0 | 50.0 | 65.0 |
| Water | 44.7 | 29.7 | 44.7 | 39.7 | 29.7 |
| Polyoxyethylene glycol (Carbowax 400) | 5.0 | — | — | — | — |
| Polyoxyethylene glycol 400 monooleate | — | 5.0 | — | 5.0 | — |
| Acetylated, ethoxylated ester-ether of lanolin alcohols (Solulan 97) | — | — | 5.0 | — | — |
| *Collagen protein hydrolysate (Stepan's Polypeptide AAS-20% active) | — | — | — | 5.0 | — |
| Lauryl lactate | — | — | — | — | 5.0 |
| Perfume, color, etc. | q.s. | q.s. | q.s. | q.s. | q.s. |

| INGREDIENT | PERCENT BY WEIGHT EXAMPLE | | |
|---|---|---|---|
| | 36 | 37 | 38 |
| JR-1L Resin | 0.1 | 0.3 | 2.0 |
| Ethyl alcohol | 50.0 | 50.0 | 50.0 |
| Water | 44.9 | 46.2 | 43.0 |
| Emcol CC-36 | 5.0 | 3.0 | 5.0 |
| Collagen protein hydrolysate (Stephan's Polypeptide LSN) | — | 0.5 | — |
| Perfume, color, etc. | q.s. | q.s. | q.s. |

| INGREDIENT | PERCENT BY WEIGHT EXAMPLE | | |
|---|---|---|---|
| | 39 | 40 | 41 |
| JR-1L Resin | 2.85 | 0.3 | 0.3 |
| Ethyl alcohol | — | 30.0 | — |
| Water | 92.15 | 44.7 | 74.7 |
| Butoxy polyoxyethylene-polyoxypropylene glycol (Ucon 50HB660) | 5.00 | 25.0 | 25.0 |
| Perfume, color, etc. | q.s. | q.s. | q.s. |

*Polypeptide LSN (Average M.W. 900 – 1500) may be used in place of Stepan's Polypeptide AAS.

The following examples further illustrate cream and lotion formulations within the scope of the present invention.

| INGREDIENT | PERCENT BY WEIGHT EXAMPLE | | |
|---|---|---|---|
| | 42 | 43 | 44 |
| JR-1L Resin | 0.3 | 0.3 | 0.3 |
| Ethyl alcohol | 60.0 | 50.0 | 50.0 |
| Water | 29.7 | 44.7 | 44.7 |
| Butoxy polyoxypropylene glycol (Ucon LB1715) | 10.0 | — | 2.5 |
| Emcol CC-36 | — | 2.5 | 2.5 |
| Butoxy polyoxyethylene-polyoxypropylene glycol |  |  |  |

-continued

| INGREDIENT | PERCENT BY WEIGHT EXAMPLE | | |
|---|---|---|---|
| | 42 | 43 | 44 |
| (Ucon 50 HB 660) | — | 2.5 | — |
| Perfume, color, etc. | q.s. | q.s. | q.s. |

| INGREDIENT | PERCENT BY WEIGHT EXAMPLE | | |
|---|---|---|---|
| | 45 | 46 | 47 |
| JR-1L Resin | 0.3 | 0.3 | 0.3 |
| Emcol CC-36 | 5.0 | 5.0 | 5.0 |
| Hexachlorophene | 0.5 | — | — |
| Salicylic acid | — | 1.0 | — |
| Benzethonium chloride | — | 0.3 | — |
| Biphenamine hydrochloride | — | — | 1.0 |
| Ethyl alcohol | 50.0 | 50.0 | 50.0 |
| Water | 44.2 | 43.4 | 43.7 |
| Perfume, color, etc. | q.s. | q.s. | q.s. |

| INGREDIENT | PERCENT BY WEIGHT EXAMPLE | | | |
|---|---|---|---|---|
| | 48 | 49 | 50 | 51 |
| JR-1L Resin | 0.5 | 0.5 | 0.5 | 0.5 |
| Emcol CC-36 | 5.0 | — | — | 5.0 |
| Isopropyl myristate | 2.0 | — | — | — |
| Glyceryl monostearate | 7.0 | 4.0 | 2.0 | 2.0 |
| Lanolin | — | 1.0 | — | — |
| N-(lauryl colaminoformyl-methyl)pyridinium chloride | — | 0.5 | — | — |
| Glycerine | — | 2.0 | — | — |
| Mineral Oil (55-65Vis) | — | 2.0 | 5.0 | 3.0 |
| Cetyl alcohol | — | 1.0 | — | — |
| Carbopol 940 | — | — | 1.0 | 1.0 |
| Triethanolamine | — | — | 1.0 | 1.0 |
| Ethoxylated (15 mol. ethylene oxide) coconut oil amine (Ethomeen C/25 Armour) | — | — | 1.0 | 1.0 |
| Water | 85.5 | 89.0 | 89.5 | 86.5 |
| Perfume, color, preservative | q.s. | q.s. | q.s. | q.s. |

What is claimed is:

1. A hair dressing composition comprising a hair-fixative quaternary cellulose ether resin having a high affinity for hair and a hair grooming agent dissolved in an aqueous alkyl alcoholic solvent in which the alkyl alcohol has from 2 to 6 carbons wherein:
   a. said resin is present in the range of from about 0.1 to 7.0% by weight based on the total weight of the composition;
   b. said hair grooming agent is present in the range of from about 1 to 60% by weight based on the total weight of the composition;
   c. the ratio of said resin to said hair grooming agent being about 1 part of resin to 10 to 30 parts of grooming agent wherein
   said resin is of the formula:

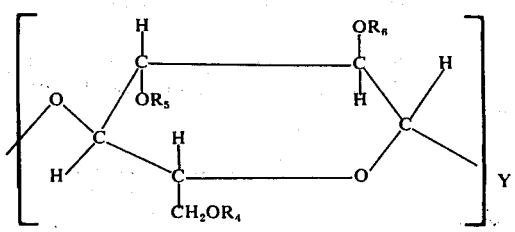

(I)

wherein:
Y indicates the degree of polymerization and is a number from 50 to 20,000;

$R_4$, $R_5$ or $R_6$ is a radical of the formula:

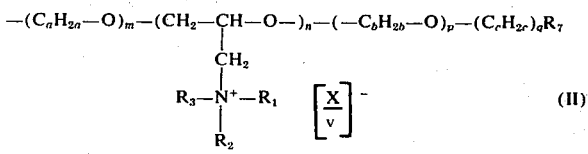

(II)

in which:
$a$ is a whole number 2 or 3;
$b$ is a whole number 2 or 3;
$c$ is a whole number 1 to 4;
$m$ is a number from 0 to 10;
$n$ is a whole number from 0 to 3;
$p$ is a whole number from 0 to 10;
$q$ is zero or 1;
$R_7$ is H or COOMe group in which Me is H, Na, K or $NH_4$;
X is a salt forming anion;
$v$ is a number equal to the valence of X;
$R_1$, $R_2$ and $R_3$ are alkyl, aryl, aralkyl, alkaryl, cycloalkyl, alkoxyalkyl or alkoxyaryl in which the alkyl moieties have up to 6 carbon atoms; the aryl moieties having up to 12 carbon atoms and the cycloalkyl moieties having 5 to 6 carbon atoms and wherein two or three of the radicals $R_1$, $R_2$ and $R_3$ may constitute a nitrogen heterocyclic nucleus having 5 to 6 atoms in the nucleus, one atom of which may also be oxygen;
wherein the resin defined by the formula I above contains the quaternary group:

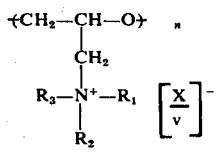

in the average of about 0.1 to 3 quaternary groups per anhydroglucose unit;
and wherein said hair grooming agent is selected from the group consisting of:
   a. polyoxypropylene triol having a molecular weight of about 1500;
   b. polyoxyethylene glycol having a molecular weight in the range of about 400 to 1000;
   c. diisopropyl adipate;
   d. diisopropyl sebacate; and
   e. protein collagen hydrolysate having a molecular weight in the range of from about 900 to 1500.

2. A composition according to claim 1 wherein said hair grooming agent is polyoxypropylene triol having a molecular weight of about 1500.

3. A composition according to claim 1 wherein said hair grooming agent is polyoxyethylene glycol having a molecular weight in the range of from about 400 to 1000.

4. A composition according to claim 1 wherein said hair grooming agent is diisopropyl adipate or diisopropyl sebacate.

5. A composition according to claim 1 wherein said hair grooming agent is protein collagen hydrolysate having a molecular weight in the range of from about 900 to 1500.

* * * * *